United States Patent [19]
LaVon et al.

[11] Patent Number: 6,015,935
[45] Date of Patent: Jan. 18, 2000

[54] ABSORBENT ARTICLES COMPRISING A MATERIAL HAVING A HIGH VERTICAL WICKING CAPACITY

[75] Inventors: Gary Dean LaVon, Middletown; Gerald Alfred Young, Cincinnati; Gregory Wade Taylor, Forest Park, all of Ohio

[73] Assignee: The Procter & Gamble Company, Cincinnati, Ohio

[21] Appl. No.: 08/825,071

[22] Filed: Mar. 27, 1997

[51] Int. Cl.$^7$ .............................. A61F 13/15; A61F 13/20
[52] U.S. Cl. ............................................. 604/378; 604/369
[58] Field of Search .................................. 604/368, 369, 604/370–378, 385.2

[56] References Cited

U.S. PATENT DOCUMENTS

| | | | |
|---|---|---|---|
| Re. 26,152 | 1/1967 | Andren . | |
| 3,592,194 | 7/1971 | Duncan | 128/287 |
| 3,860,003 | 1/1975 | Buell . | |
| 4,413,996 | 11/1983 | Taylor | 604/382 |
| 4,531,945 | 7/1985 | Allison | 604/378 |
| 4,610,678 | 9/1986 | Weisman et al. | 604/368 |
| 4,699,619 | 10/1987 | Bernardin | 604/378 |
| 4,756,709 | 7/1988 | Stevens | 604/385.2 |
| 4,826,499 | 5/1989 | Ahr | 604/385.2 |
| 4,834,736 | 5/1989 | Boland et al. | 604/385.2 |
| 4,842,594 | 6/1989 | Ness | 604/368 |
| 4,880,419 | 11/1989 | Ness | 604/368 |
| 4,994,037 | 2/1991 | Bernardin | 604/368 |
| 5,098,423 | 3/1992 | Pieniak et al. | 604/385.1 |
| 5,147,345 | 9/1992 | Young et al. | 604/378 |
| 5,260,345 | 11/1993 | DesMarais et al. | 521/148 |
| 5,360,419 | 11/1994 | Chen et al. | 604/368 |
| 5,387,207 | 2/1995 | Dyer et al. | 604/369 |
| 5,800,416 | 9/1998 | Seger et al. | 604/366 |
| 5,843,852 | 12/1998 | Dutkiewicz et al. | 442/334 |
| 5,853,402 | 12/1998 | Faulks et al. | 604/378 |

FOREIGN PATENT DOCUMENTS

| | | | |
|---|---|---|---|
| 0 410 480 B1 | 1/1991 | European Pat. Off. . | |
| 0 439 012 A2 | 7/1991 | European Pat. Off. | A61F 13/15 |
| 0 692 232 A1 | 1/1996 | European Pat. Off. | A61F 13/15 |
| 2 145 661 | 4/1985 | United Kingdom | B32B 5/22 |
| 2 165 757 | 4/1986 | United Kingdom | A41B 13/02 |
| 2 295 321 | 5/1996 | United Kingdom | A61F 13/46 |
| WO 95/17870 | 7/1995 | WIPO | A61F 13/15 |
| WO 96/19169 | 6/1996 | WIPO | A61F 13/15 |
| WO 98/22065 | 5/1998 | WIPO . | |
| WO 98/22067 | 5/1998 | WIPO . | |

Primary Examiner—Mickey Yu
Assistant Examiner—Tram A. Nguyen
Attorney, Agent, or Firm—Carl J. Roof; Kevin D. Hogg; Steven W. Miller

[57] ABSTRACT

Disclosed are absorbent cores for inclusion in articles such as diapers, incontinent briefs, training pants, diaper holders and liners, feminine hygiene garments, and the like, designed to provide improved fit and comfort for the wearer while adequately containing body exudates. The absorbent core is designed so as to retain low levels of fluid in the crotch region, relative to the other core regions, even when the core absorbs significant amounts of fluid during use. To achieve this, the absorbent core is designed such that fluid is moved substantially from the crotch region to the front and/or rear ends of the article. In particular, the absorbent core comprises in its crotch region a material having significant vertical wicking absorbent capacities.

48 Claims, 4 Drawing Sheets

ABSORBENT ARTICLES COMPRISING A MATERIAL HAVING A HIGH VERTICAL WICKING CAPACITY

FIELD OF THE INVENTION

The present invention relates to absorbent articles such as diapers, incontinent briefs, training pants, diaper holders and liners, sanitary hygiene garments, and the like, and more particularly, to absorbent articles providing improved fit when wetted with body fluids. Improved fit is achieved by utilizing a material having a high vertical wicking capacity.

BACKGROUND OF THE INVENTION

Infants and other incontinent individuals wear absorbent articles such as diapers to absorb and retain urine and other body exudates. Absorbent articles function both to contain the discharged materials and to isolate these materials from the body of the wearer and from the wearer's garments and bed clothing. Disposable absorbent articles having many different basic designs are known in the art. For example, U.S. Pat. Re. 26,151, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elastic leg cuff disposable diaper which has achieved wide acceptance and commercial success.

Many diaper designs are relatively wide and bulky, when dry and particularly when wet, in the region of the article that fits between the legs of the wearer. This results in a certain level of discomfort to the wearer, as these diapers tend to bunch when worn. In an effort to address wearer discomfort, U.S. Pat. No. 4,610,678 (Weisman et al.) describes diapers comprising densified cores that are narrower in this region than were prior designs. Nonetheless, even these articles store significant levels of absorbed fluids in the discharge region of the article. This discharge region is positioned within the portion of the article that fits in the wearer's crotch region when worn.

Since prior absorbent articles do not effectively distribute fluid, these articles are typically designed to store significant quantities of fluid in the crotch region of the diaper. Thus, upon each loading, this region of the article becomes increasingly bulky and therefore tends to be more uncomfortable for the wearer. See, for example, U.S. Pat. No. 5,098,423 to Pieniak et al., which builds on the disclosure of the Weisman patent, and describes a low dry bulk disposable diaper. The focus of the '423 patent is an article having a relatively low cross sectional area, when dry, particularly in the "impact zone" (defined in the patent as the second and third fifths of the article's length). Indeed, an important aspect of the described articles is the ability of the absorbent material in the impact zone to absorb fluid. The patent specifically indicates that at least 60% of the total absorbed fluid is retained in the diaper's impact zone. Thus, while the patent discusses the desire for improved fit when dry, it fails to provide an article having improved fit and comfort throughout the entire wearing period. Moreover, the primary consideration for improving fit is on thin and wide structures which fold and bunch during use, rather than optimizing narrowness and bulk, dry and wet, of the absorbent material in the crotch region. Accordingly, the articles described in the '423 patent have an overall low cross sectional area when dry, accomplished by providing a relatively thin (i.e., in the article's the z-dimension), relatively wide (i.e., in the article's x-dimension) core, with 60% of the absorbent capacity in the crotch region. This results in reduced comfort when the article is wetted with body fluid.

It therefore would be advantageous to provide an absorbent article that provides better fit and wearer comfort, even after the article is wetted with body fluids. It would be further advantageous to provide an absorbent article which has reduced bulk in the crotch region in both the dry and wet states.

Therefore, it is an object of the present invention to provide an absorbent article providing increased comfort for the wearer by including in the crotch region of the article a material having a vertical wicking capacity such that the material readily distributes a significant amount of fluid remote from the crotch region.

It is a further object of the present invention to provide an absorbent article having improved fit on the wearer during use by reducing the relative amount of fluid retained in the article's crotch region.

These and other objects of the present invention will be more readily apparent when considered in reference to the following description and when taken in conjunction with the accompanying drawings.

SUMMARY OF THE INVENTION

The present invention provides absorbent articles such as diapers, incontinent briefs, training pants, diaper holders and liners, feminine hygiene garments, and the like, designed to provide improved fit and comfort for the wearer while adequately containing body exudates. Such an absorbent article has a containment assembly (chassis) comprising an outer covering layer typically comprising a liquid pervious topsheet and a liquid impervious backsheet, and an absorbent core associated with the outer covering layer. The absorbent core is designed so as to retain low levels of fluid in the crotch region, relative to the other core regions, even when the core absorbs significant amounts of fluid during use. To achieve this, the absorbent core is designed such that fluid is moved substantially from the crotch region to the front and/or rear ends of the article.

In one aspect, the present invention relates to an absorbent article comprising an absorbent core having a crotch region, wherein (i) the crotch region has an absorbent capacity of not more than about 40% of the absorbent core's total absorbent capacity and (ii) the crotch region comprises a material having a vertical wicking capacity of at least about 15 g/g at a height of 2 cm. The present invention further relates to an absorbent article comprising an absorbent core having a crotch region, wherein (i) the crotch region has an absorbent capacity of not more than about 40% of the absorbent core's total absorbent capacity and (ii) the crotch region comprises a material having a vertical wicking capacity of at least about 10 g/g at a height of 20 cm. In another aspect, the invention relates to an absorbent article comprising an absorbent core having a crotch region, wherein (i) the crotch region has an absorbent capacity of not more than about 40% of the absorbent core's total absorbent capacity and (ii) the crotch region comprises a material having a vertical wicking capacity of at least about 5 g/g at a height of 25 cm. In another aspect, the invention relates to an absorbent article comprising an absorbent core having a crotch region, wherein (i) the crotch region has an absorbent capacity of not more than about 40% of the absorbent core's total absorbent capacity and (ii) the crotch region comprises a material having a vertical wicking capacity of at least about 0.5 g/g at a height of 30 cm. In yet another aspect, the invention relates to an absorbent article comprising an absorbent core having a cross sectional area at the core's crotch point of not more than about 1.3 cm², wherein the crotch region comprises a material having a vertical wicking capacity of at least about 10 g/g at a height of 20 cm.

BRIEF DESCRIPTION OF THE DRAWINGS

While the specification concludes with claims particularly pointing out and distinctly claiming the subject matter which is regarded as forming the present invention, it is believed that the invention will be understood from the following description which is taken in conjunction with the accompanying drawings in which like designations are used to designate substantially identical elements, and in which:

DETAILED DESCRIPTION OF THE INVENTION

Figure 1:
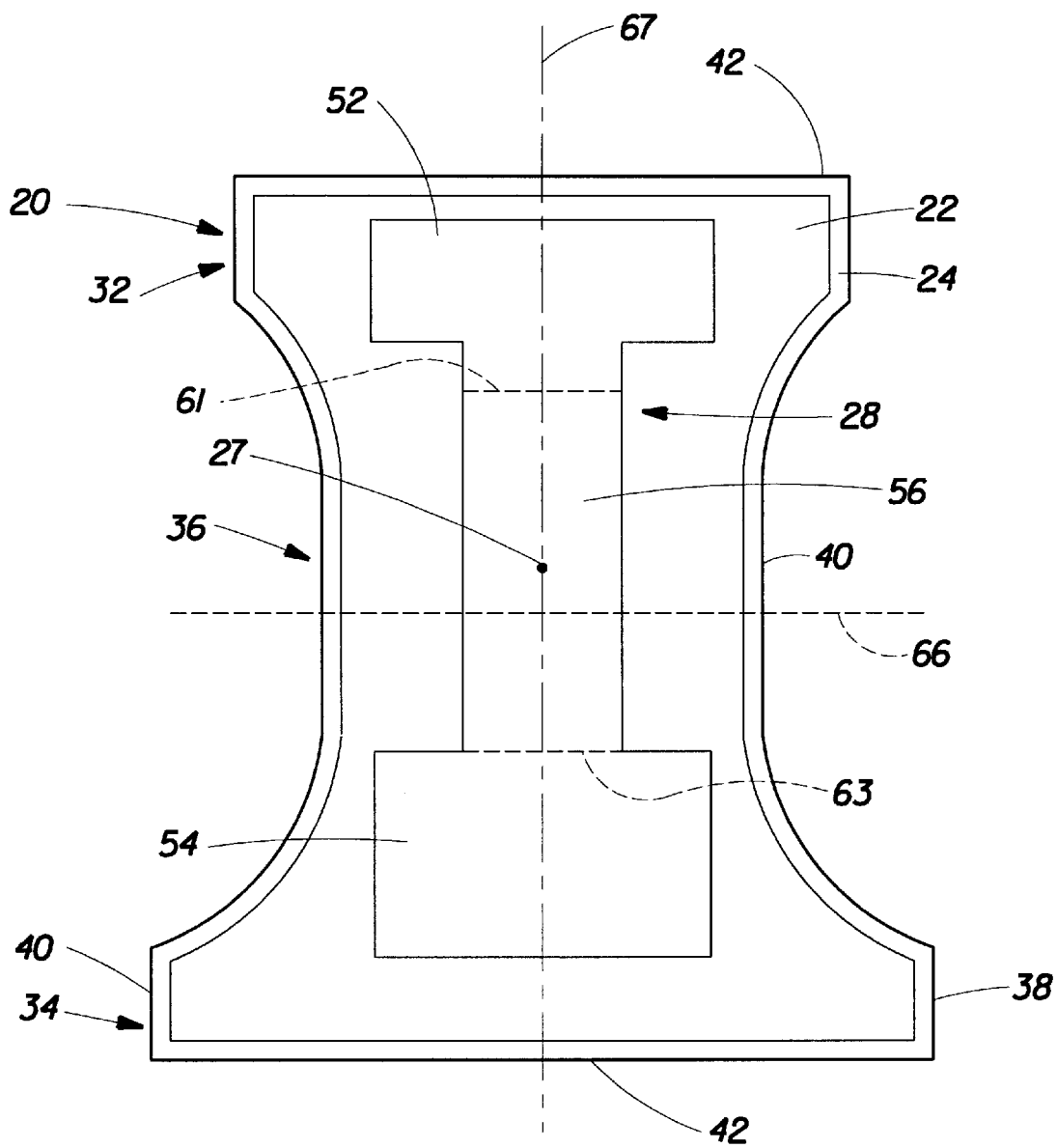
FIG. 1 is a top plan view of an absorbent article according to the present invention where the topsheet is transparent so as to more clearly show the absorbent core.

As used herein, the term "absorbent article" refers to devices which absorb and contain body exudates, and, more specifically, refers to devices which are placed against or in proximity to the body of the wearer to absorb and contain the various exudates discharged from the body. Absorbent articles include devices designed to absorb urine, which are used by incontinent persons. Such incontinent articles include but are not limited to diapers, adult incontinent briefs, training pants, diaper holders and liners. Other absorbent articles include those designed to absorb blood-based fluids such as menses. Such sanitary hygiene articles include tampons, catamenial pads, and the like. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

As used herein, the term "absorbent core" refers to the portions (e.g., layers) of an absorbent article which function to acquire, distribute, transfer, store and/or redistribute fluid. Acquisition materials include materials whose primary function is to acquire then relinquish fluids. Such materials include acquisition layers, topsheet materials, transfer layers, flow control modules, wrap tissues or nonwoven sheets designed to prevent migration of hydrogel forming polymers, etc. As used herein, the term "distribution material" refers to the absorbent core material(s) whose primary function is to absorb and distribute/redistribute fluid to points away from the point of initial fluid loading. As used herein, the term "storage material" refers to the absorbent core material that retains a majority of the fluid retained, on a weight basis. It should be understood that the terms "distribution material" and "storage material" are not mutually exclusive. In certain embodiments, a single material may function to provide both fluid distribution and fluid storage.

As used herein, the term "front" refers to the portion of an article or absorbent core that is intended to be positioned proximate the front of a wearer. The term "rear" refers to the portion of an article or absorbent core that is intended to be positioned proximate the back of the wearer. As such, use of the relative term "in front of" means a position in the article or core more toward the front of the article or core, while the term "behind" means a position in the article or core more toward the rear of the article or core.

As used herein, the term "z-dimension" refers to the dimension orthogonal to the length and width of the member, core or article. The z-dimension corresponds generally to the thickness of the member, core or article.

As used herein, the term "x-y dimension" refers to the plane orthogonal to the thickness of the member, core or article. The x- and y-dimensions correspond generally to the width and length, respectively, of the member, core or article.

The "crotch point" of an article and the article's absorbent core is determined by placing the article on a wearer in a standing position and then placing an extensible filament around the legs in a figure eight configuration. (See FIG. 4.) The point in the article and the absorbent core corresponding to the point of intersection of the filament is deemed to be the crotch point of the article and the absorbent core. It is understood that the crotch point is determined by placing the absorbent article on a wearer in the intended manner and determining where the crossed filament would contact the article/core.

As referred to herein, the "crotch region" of an absorbent core corresponds to 50% of the absorbent core's total length (i.e., in the y-dimension), where the crotch point is located in the longitudinal center of the crotch region. That is, the crotch region is determined by first locating the crotch point of the absorbent core, and then measuring forward and backward a distance of 25% of the core's total length.

As used herein, the term "crotch width" refers to the width in the crotch region of the absorbent core layer that retains the most fluid when the article is loaded to 70% of the articles total capacity via the Fluid Acquisition method described below. When this layer consists of a plurality of discrete layers, the layer having the smallest width is the width of that layer, and therefore is the crotch width of the absorbent core. If a layer is profiled in the cross (x-) dimension, the width of the layer is determined by the width of the highest basis weight region of the profile. A method for determining crotch width is described in the Test Methods section below.

As used herein, the term "crotch cross sectional area" refers to the dry cross sectional area in the crotch region of the absorbent core layer that retains the most fluid when the article is loaded to 70% of the articles total capacity via the Fluid Acquisition method described below. When this layer consists of a plurality of discrete layers, the width and caliper of each of the layers is measured and the sum of their individual cross sectional areas is the crotch region cross sectional area. A method for determining crotch width is described in the Test Methods section below.

As used herein, the term "layers" refers to identifiable components of the absorbent structure, and any structure referred to as a "layer" may actually comprise a laminate or combination of several sheets or webs of the requisite type of materials as hereinafter described. As used herein, the term "layer" includes the terms "layers" and "layered." For purposes of this invention, it should also be understood that the term "upper" refers to the layer of the absorbent core which is nearest to and faces the article topsheet; conversely, the term "lower" refers to the layer of the absorbent core which is nearest to and faces the article backsheet. It should be noted that the various members, layers, and structures of absorbent articles according to the present invention may or may not be generally planar in nature, and may be shaped or profiled in any desired configuration.

An embodiment of an absorbent article in the form of a diaper 20 having one such absorbent core according to the present invention is shown in FIG. 1. FIG. 1 is a top plan view of diaper 20 in a flat-out, uncontracted state (i.e., with any elastic-induced contraction removed) having a topsheet 22, a backsheet 24, and an absorbent core indicated generally as 28 that is positioned between topsheet 22 and backsheet 24. Topsheet 22 is shown as being transparent so as to better illustrate the absorbent core 28.

As also shown in FIG. 1, diaper 20 has a front waistband region 32, a back waistband region 34, a center region 36 and a periphery 38 that is defined by the outer edge of backsheet 24 and which has longitudinal edges designated 40 and end edges designated as 42. The longitudinal axis of diaper 20 runs essentially parallel to longitudinal edges 40 and is depicted as longitudinal centerline 67 (and corresponds to the y-direction or length), while the transverse axis runs essentially parallel to end edges 42 and is depicted as transverse centerline 66 (and corresponds to the x-direction or width). The waistband regions 32 and 34 comprise those upper portions of the diaper 20, which when worn, encircle the waist of the wearer. The center region 36 is that portion of the diaper 20 between waistband regions 32 and 34, and comprises that portion of the diaper 20 which when worn, is positioned between the legs of the wearer and covers the lower torso of the wearer. Thus, the center region 36 defines the area of typical liquid deposition for a diaper 20 or other disposable absorbent article.

Topsheet 22 and backsheet 24 can be associated together in any suitable manner. As used herein, the term "associated" encompasses configurations where topsheet 22 is directly joined to backsheet 24 by affixing the topsheet directly to the backsheet, and configurations where the topsheet is indirectly joined to the backsheet by affixing the topsheet to intermediate members which in turn are affixed to the backsheet. Preferably, the topsheet 22 and backsheet 24 are affixed directly to each other by attachment means (not shown) such as an adhesive or any other attachment means as known in the art. For example, a uniform continuous layer of adhesive, a patterned layer of adhesive, or an array of separate lines or spots of adhesive may be used to affix topsheet 22 to backsheet 24. As shown in FIG. 1, topsheet 22 has a slightly smaller size configuration than backsheet 24. However, topsheet 22 and backsheet 24 can both have the same size configuration (i.e., are coextensive) such they are joined together at periphery 38 of diaper 20. The size of the backsheet 24 is dictated in part by the size of the absorbent core 28 and the exact diaper design selected. In the embodiment shown in FIG. 1, the backsheet 24 has an hourglass-shaped configuration. However, other configuration such as rectangular, I-shaped and the like are also suitable.

Although not shown, diaper 20 can have elastic members that exert a contracting force on the diaper so that it configures more closely and more comfortably to the wearer. These elastic members can be assembled in a variety of well known configurations, such as those described generally in U.S. Pat. No. 3,860,003 (Buell), issued Jan. 14, 1975, which patent is incorporated by reference. The elastic members can be disposed adjacent the periphery 38 of the diaper 20, preferably along each longitudinal edge 40, so that the elastic members tend to draw and hold the diaper 20 against the legs of the wearer. Alternatively, the elastic members can be disposed adjacent either or both of the end edges 42 of diaper 20 to provide a waistband as well as or rather than leg cuffs. See, for example, U.S. Pat. No. 4,515,595 (Kievit et al), issued May 7, 1985, which is incorporated by reference. The elastic members are secured to the diaper 20 in an elastically contractible condition so that in a normally unrestrained configuration, these elastic members effectively contract or gather the diaper 20. The elastic members can be secured in an elastically contractible condition in at least two ways. For example, the elastic members can be stretched and secured while the diaper 20 is in an uncontracted condition. Alternatively, the diaper 20 can be contracted, for example, by pleating, and the elastic members secured and connected to the diaper 20 while they are in their unrelaxed or unstretched condition. The elastic members can extend essentially the entire length of the diaper 20 in the center region 36, or alternatively can extend the entire length of the diaper 20, or any other length suitable to provide an elastically contractible line. The length of these elastic members is typically dictated by the diaper's design.

Referring to FIG. 1, absorbent core 28 is depicted in an "I" configuration. As is indicated above, the absorbent core will comprise front and rear regions, as well as a crotch region. These regions are defined by determining the crotch point of core 28 in accordance with the description herein. As discussed above, the crotch point is determined by reference to the wearer's anatomy. For purposes of illustration only, the crotch point of core 28 is depicted as item 27 in FIG. 1. Crotch point 27 is depicted as being located on the longitudinal centerline 67 of diaper 20 and absorbent core 28. This will generally be the case, regardless of the configuration of the diaper and absorbent core. However, as indicated, crotch point 27 is not located on transverse centerline 66 in this particular embodiment, though it may be in other diaper/core designs. As is discussed above, once the crotch point of absorbent core 28 is determined, the crotch region is determined by measuring forward from the crotch point a distance of 25% of the core's total length (depicted as transverse line 61) and backward from the crotch point a distance of 25% of the core's total length (depicted as transverse line 63). In this illustration, the crotch region is the region of the core located between transverse lines 61 and 63. As depicted in FIG. 1, absorbent core 28 is shown to have a front region 52, a back region 54, and a crotch region 56. Again, the crotch region 56 of core 28 is dictated by the location of the crotch point in the core.

The topsheet 22 is compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet is made of a hydrophobic material to isolate the wearer's skin from liquids contained in the absorbent core that is treated on at least one side with a surfactant to allow liquids to readily penetrate through its thickness.

In a preferred embodiment of the present invention, at least a portion of the topsheet is subjected to mechanical stretching in order to provide a "zero strain" stretch laminate that forms the elastic side panels. Thus, the topsheet is preferably elongatable, most preferably drawable, but not necessarily elastomeric, so that the topsheet will, upon mechanical stretching, be at least to a degree permanently elongated such that it will not fully return to its original configuration. In preferred embodiments, the topsheet can be subjected to mechanical stretching without undue rupturing or tearing of the topsheet. Thus, it is preferred that the topsheet have a low cross-machine direction (lateral direction) yield strength.

There are a number of manufacturing techniques which may be used to manufacture the topsheet. For example, the topsheet may be a nonwoven web of fibers. When the topsheet comprises a nonwoven web, the web may be spunbonded, carded, wet laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 in). Preferably, the topsheet has a basis weight from about 18 to about 25 g/m$^2$. A suitable topsheet is manufactured by Veratec, Inc., a division of International Paper Company, of Walpole, Mass. under the designation P-8.

The topsheet 22 is positioned above the body surface of the absorbent core 28. In preferred embodiments, and acquisition material is positioned between absorbent core 28 and topsheet 22. Topsheet 22 is preferably joined thereto and to the backsheet 24 by attachment means (not shown) such as those well known in the art. Suitable attachment means are described below with respect to joining the backsheet 24 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet and the backsheet are joined directly to each other in the diaper periphery and are indirectly joined together by directly joining them to the absorbent core by the attachment means (not shown). In an alternative embodiment, the absorbent core (or the preferred acquisition material) need not be joined to either the topsheet or the backsheet such that the absorbent core is allowed to "float" between them.

The backsheet 24 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the diaper such as bedsheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mils) to about 0.051 mm (2.0 mils).

In a preferred embodiment of the present invention, at least a portion of the backsheet is subjected to mechanical stretching in order to provide both a "zero strain" stretch laminate that forms the elastic side panels and, if desired, to prestrain the portion of the backsheet coinciding with the elastic waist feature or any other elastic feature. Thus, the backsheet is preferably elongatable, most preferably drawable, but not necessarily elastomeric, so that the backsheet will, upon mechanical stretching, be at least to a degree permanently elongated such that it will not fully return to its original undistorted configuration. In preferred embodiments, the backsheet can be subjected to mechanical stretching without undue rupturing or tearing. Thus, it is preferred that the backsheet have an ultimate elongation to break of at least about 400% to about 700% in the cross-machine direction as measured using a method consistent with ASTM D-638. Thus, preferred polymeric films for use as the backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Ind. under the designations X-8323, RR8220 blend for certain blown films, and RR5475 blend for certain cast films.

The backsheet 24 is preferably embossed (typically, to a caliper of about 0.127 mm (5.5 mils)) and/or matte finished to provide a more clothlike appearance. Further, the backsheet may permit vapors to escape from the absorbent core (i.e., breathable) while still preventing exudates from passing through the backsheet.

The backsheet 24 is positioned adjacent the lower surface of the absorbent core 28 and is preferably joined thereto by attachment means (not shown) such as those well known in the art. Alternatively, an additional material (e.g., acquisition material) may be placed between the backsheet 24 and the absorbent core 28. For example, the backsheet 24 may be secured to the absorbent core 28 or any intervening material by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H.B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waist-Containment Garment" which issued to Minetola and Tucker on Mar. 4, 1986. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

Figure 2:
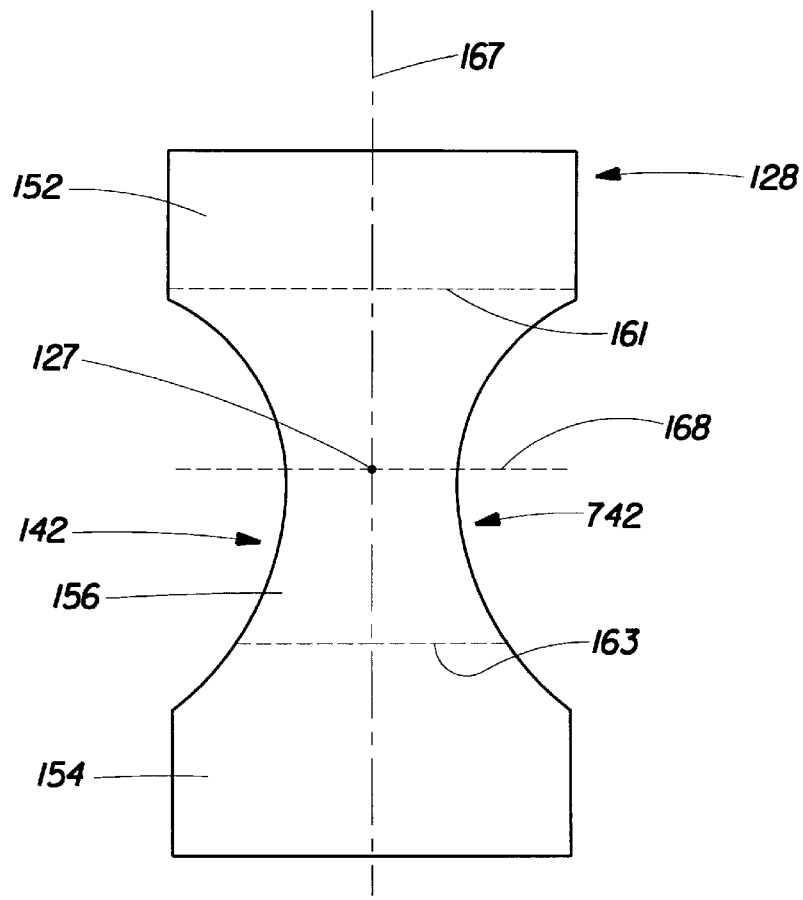
FIG. 2 is a plan view of a preferred absorbent core of the present invention.

The absorbent core 28 will comprise any absorbent means which is capable of absorbing and retaining liquids such as urine and other certain body exudates, and which is capable of providing the fluid distribution/storage properties which define the present invention. While absorbent core 28 is depicted in FIG. 1 in an "I" configuration, any shape may be utilized. For example, an absorbent core 128 is shown in FIG. 2 in an "hour glass" configuration, wherein the core has arcuate cutouts in its longitudinal edges, indicated generally as 142. Similary, in FIG. 3, core 228 has arcuate cutouts 242 in its lonitudinal edges. For illustration purposes, the crotch point is identified by item 127. (As discussed above, the crotch point of the absorbent core is extrapolated from the wearer.) As shown, the crotch point 127 generally lies on longitudinal center line 167 and on transverse line (though not the center transverse line in this embodiment) 168. The crotch region is determined by measuring forward from the crotch point a distance of 25% of the core's total length (depicted as transverse line 161) and backward from the crotch point a distance of 25% of the core's total length (depicted as transverse line 163). The crotch region 156, is the region of the core between transverse lines 161 and 163. In addition to crotch region 156, core 128 has a front region 152 and a rear region 154.

Figure 3:
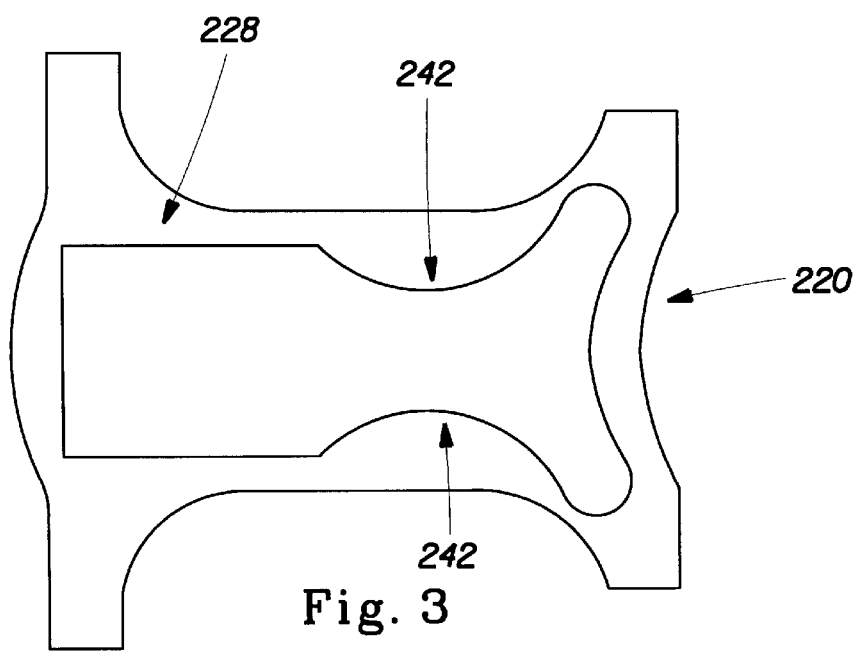
FIG. 3 is a plan view of another absorbent core of the present invention.

FIG. 3 illustrates another diaper and corresponding core configuration. In particular, diaper 220 is configured so as to fit within the low motion zone of the wearer. (A disclosure of low motion articles and corresponding cores is described in detail in U.S. Pat. No. 5,358,500 to LaVon et al., the disclosure of which is incorporated herein by reference.) The absorbent core, depicted generally as 228, is also configured so as to fit within the low motion zone of the wearer.

Figure 4:
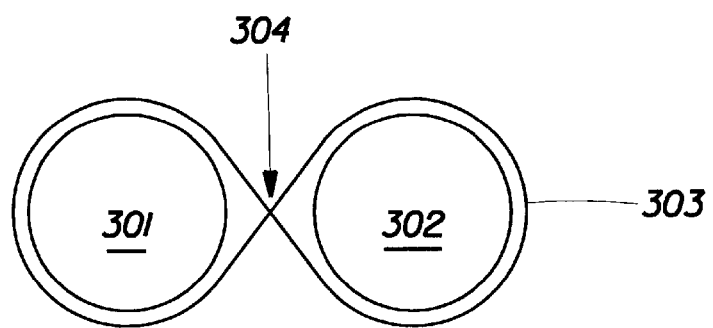
FIG. 4 illustrates how the crotch point of a wearer, an absorbent article and the corresponding absorbent core are determined.

FIG. 4 illustrates the means for determining the crotch point of an article and its absorbent core. Referring to FIG. 4, the legs of a standing wearer are depicted crossectionally as 301 and 302. A continuous material 303 (e.g., a string or rubberband) is twisted once and is placed around the wearer's legs at a point sufficiently close to the wearer's torso such that the intersection 304 of material 303 can be extrapolated onto the article being worn. The crotch point of the core of the article is thereby determined, and the crotch region of the core is determined per the above description.

The crotch width of the absorbent core, when dry and when wet, is also important in providing improved fit on the wearer. It is preferred that the crotch width be small, even when wetted with fluid, so that the absorbent core undergoes minimal bunching when the wearer's legs are closed. In this regard, the absorbent cores useful in the present invention will preferably have a crotch width when dry and when wet of not more than about 7 cm. Preferably, the crotch width when dry and when wet will be not more than about 6 cm, still more preferably not more than about 5 cm. The means for measuring crotch width is described in Test Methods section, infra. It is further preferred that at the crotch point of the absorbent core, the core have a relatively small cross sectional area (x-dimension times z-dimension). In this regard, the absorbent cores useful in the present invention will preferably have a crotch cross sectional area, when dry, of not more than about 2.6 cm². Preferably, the crotch cross sectional area, when dry, will be not more than about 1.8 cm², more preferably not more than about 1 cm², still more preferably not more than about 0.6 cm² and most preferably not more than about 0.4 cm². The means for measuring cross sectional area is described in the Test Methods section, infra.

It follows that a reduction in cross sectional area and/or crotch width of an absorbent core with a uniform capacity per unit surface area necessarily reduces the amount of material available in the zone of typical liquid deposition. Prior attempts to improve fit by reducing width in the crotch region did so by increasing capacity per unit surface area so as to maintain the necessary capacity in the crotch region. Such prior attempts utilized additional fiber in the crotch region for liquid absorption and in some instances additional hydrogel-forming polymers for liquid storage. These approaches therefore result in a negative impact on bulk both dry and wet. In direct contrast, the present invention is based on moving the fluid deposited in the crotch region away from that region. This is reflected in a reduced level of fluid storage in the crotch region of the absorbent core. As such, the crotch region of the absorbent core will comprise material(s) that function to distribute fluids away from the crotch region. (While fluid distribution is an important function of the core's crotch region material, it is within the scope of the invention to include materials in the crotch region whose primary function is the storage of fluids, so long as the requisite properties of the present invention are achieved.) In particular, the absorbent core's of the present articles will comprise a material that exhibits high vertical wicking capacity. The ability to wick fluid vertically, i.e., fluid wicking in a direction opposite gravitational forces, is an important performance attribute since the absorbent cores are utilized in absorbent articles in a manner such that fluid to be absorbed must be moved within the article from a relatively lower position to a relatively higher position within the absorbent core of the article. This ability to move fluid against gravity is of particular import to the present invention, given that relatively small levels of fluid are to be stored in the crotch region of the core.

In this regard, the absorbent cores will comprise a fluid material having a vertical wicking capacity of at least about 15 g/g, preferably at least about 25 g/g, still more preferably at least about 40 g/g, at a height of 2 cm. Alternatively, the absorbent core will comprise a material having a vertical wicking absorbent capacity at a height of 20 cm of at least about 10 g/g, preferably at least about 20 g/g, more preferably at least about 30 g/g, still more preferably at least about 40 g/g. Alternatively, the material will have a vertical wicking absorbent capacity at a height of 25 cm of at least about 5 g/g, preferably at least about 15 g/g, more preferably at least about 20 g/g, still more preferably at least about 30 g/g. Alternatively, the material will have a vertical wicking absorbent capacity at a height of 30 cm of at least about 0.5 g/g, preferably at least about 10 g/g, more preferably at least about 20 g/g, still more preferably at least about 30 g/g. It should be understood that while the above definitions are provided in the alternative, a single material may possess more than one of these attributes.

The absorbent articles of the present invention will also comprise an absorbent core that at equilibrium retains less than about 40% of the absorbent core's total capacity in the crotch region of the core. Of course, the storage of smaller amounts of fluid in the core's crotch region, relative to the front/rear regions of the core, is a reflection of the ability of the core materials to move fluid out of the crotch region during wear, and thereby improve fit and wearer comfort. In this regard, the absorbent core's useful in the present invention will preferably retain less than about 25%, more preferably less than about 15%, still more preferably from 0 to about 10%, of the core's total capacity at equilibrium in the core's crotch region.

As discussed above, the absorbent core will comprise a material which functions to distribute fluid out of the core's crotch region. In one embodiment, the absorbent core will comprise the same material in the front and rear of the core as is contained in the crotch region thereof. That is, the distribution material will also be suitable for fluid storage. Alternatively, the core can contain a distinct, higher capillary suction storage material in the front and/or rear regions of the core. This storage material will then desorb the relatively lower capillary suction distribution materials.

A preferred absorbent material for providing the requisite wicking properties is an open-celled absorbent polymeric foam material that is derived by polymerizing a High Internal Phase Water-in-Oil Emulsion (hereafter referred to a HIPE). Such polymeric foams may be formed to provide the requisite storage properties, as well as the requisite distribution properties. Where distinct storage materials are included in the front and rear sections of the core, the polymeric distribution foams will preferably exhibit desorption properties that allow these other core components (having higher absorption pressures than the desorption pressure of the distribution foam) to partition away fluid. It is desirable that this component keep the wearer's skin dry, even in "gush" situations and even when subjected to a compressive load; is soft, flexible and comfortable to the wearer of the absorbent article; and has a relatively high capacity for fluid so as to provide diapers and other absorbent articles that efficiently utilize core components.

HIPE-derived foams which provide the requisite distribution properties for use herein are described in copending U.S. patent application Ser. No. 08/563,866 (DesMarais et al.), filed Nov. 25, 1995 (hereafter referred to as "'866 application"); U.S. Pat. No. 5,387,207 (Dyer et al.), issued Feb. 7, 1995; and U.S. Pat. No. 5,260,345 (DesMarais et al.), issued Nov. 9, 1993; the disclosure of each of which is hereby incorporated by reference.

Polymeric foams useful in the present invention are those which are relatively open-called. This means the individual cells of the foam are in communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2 in the '866 application. As used herein, a foam material is "open-celled" if at least 80% of the cells in the foam structure that are at least 1 $\mu$m in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures.

The polymeric foams can be prepared in the form of collapsed (i.e. unexpanded), polymeric foams that, upon contact with aqueous fluids, expand and absorb such fluids. See, for example, copending U.S. patent application Ser. No. 08/563,866 and U.S. Pat. No. 5,387,207. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state. Non-collapsible foams, such as those described copending U.S. patent application Ser. No. 08/542,497 and U.S. Pat. No. 5,260,345 are also useful as the distribution material.

An important parameter of these foams is their glass transition temperature. The Tg represents the midpoint of the transition between the glassy and rubbery states of the polymer. Foams that have a higher Tg than the temperature of use can be very strong but will also be very rigid and potentially prone to fracture. When such foams are collapsible, they also typically take a long time to recover to the expanded state when wetted with aqueous fluids colder than the Tg of the polymer after having been stored in the collapsed state for prolonged periods. The desired combination of mechanical properties, specifically strength and resilience, typically necessitates a fairly selective range of monomer types and levels to achieve these desired properties.

It has been found that the specific surface area per foam volume of the polymeric foam is particularly useful for empirically defining foam structures that will remain in a collapsed state. Furthermore, this property is important to the material's ability to provide the vertical wicking absorbent capacities discussed herein. See U.S. Pat. No. 5,387,207, where specific area per foam volume is discussed in detail. "Specific surface area per foam volume" refers to the capillary suction specific surface area of the foam structure times its foam density in the expanded state. Polymeric foams having specific surface area per foam volume values of at least about 0.025 m$^2$/cc, more preferably at least about 0.05 m$^2$/cc, most preferably at least about 0.07 m$^2$/cc, have been found empirically to remain in a collapsed state, and are therefore preferred herein.

Another important property of the absorbent polymer foams useful herein is their free absorbent capacity. "Free absorbent capacity" is the total amount of test fluid (synthetic urine) which a given foam sample will absorb into its cellular structure per unit mass of solid material in the sample. To be especially useful in the absorbent articles of the present invention, the absorbent foams should have a free absorbent capacity of from about 55 to about 100 mL, preferably from about 55 to about 75 mL of synthetic urine per gram of dry foam material. The procedure for determining the free absorbent capacity of the foam is described in the TEST METHODS section of the '866 application.

Upon exposure to aqueous fluids, collapsible foams useful herein expand and absorb the fluids. When these foams are compressively dewatered to a thickness of about 1/6 (17%) or less of their fully expanded thickness, they remain in a very thin state, with a concomitant increase in storage efficiency and flexibility. This is attributable to the low density of the expanded foams. The "expansion factor" for these foams is at least about 4X, i.e. the thickness of the foam in its expanded state is at least about 4 times the thickness of the foam in its collapsed state. The collapsed foams of the present invention typically have an expansion factor in the range of from about 4X to about 10X. By comparison, prior higher density foams typically have an expansion factor of only 4X to 5X.

For the purposes of the present invention, the relationship between expanded and collapsed thickness for compressively dewatered foams can be empirically approximated from the following equation:

$$\text{thickness}_{expanded} = \text{thickness}_{collapsed} \times 0.133 \times \text{W:O ratio}$$

where "thickness$_{expanded}$" is the thickness of the foam in its expanded state;

"thickness$_{collapsed}$" is the thickness of the foam in its collapsed state;

and "W:O ratio" is the water-to-oil ratio of the high internal phase emulsion from which the foam is made. Thus, a typical foam made from an emulsion with water-to-oil ratio of 60:1 would have a predicted expansion factor of 8.0, i.e., an expanded thickness 8 times the collapsed thickness of the foam. The procedure for measuring the expansion factor is described in the TEST METHODS section of the '866 application.

An important mechanical feature of the absorbent polymeric foams useful in the present invention is their strength in their expanded state, as determined by its resistance to compression deflection (RTCD). The RTCD exhibited by the foams is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as absorbents in absorbent articles such as diapers, the foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams of the present invention can be quantified by determining the amount of strain produced in a sample of saturated foam held under a certain confining pressure for a specified temperature and period of time. The method for carrying out this particular type of test is described in the TEST METHODS section of the '866 application. Foams useful as absorbents are those which exhibit a RTCD such that a confining pressure of 5.1 kPa produces a strain of typically about 40% or less compression of the foam structure when it has been saturated to its free absorbent capacity with synthetic urine having a surface tension of 65±5 dynes/cm. Preferably the strain produced under such conditions will be in the range from about 2 to about 25%, more preferably from about 2 to about 15%, most preferably from about 2 to about 10%.

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique, however, for determining cell size in foams involves a simple measurement based on the scanning electron photomicrograph of a foam sample. The cell size measurements given herein are based on the number average cell size of the foam in its expanded state. The foams useful as absorbents for aqueous fluids in accordance with the present invention will preferably have a number average cell size of about 50 $\mu$m or less, and typically from about 5 $\mu$m to 35 $\mu$m.

"Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the TEST METHODS section of U.S. Pat. No. 5,387,207 is one method that can be employed for density determination. In its collapsed state, polymeric foams of the present invention useful as absorbents have dry basis density values in the range of from about 0.1 to about 0.2 g/cc, preferably from about 0.11 to about 0.15 g/cc, and most preferably from about 0.12 to about 0.14 g/cc. In its expanded state, polymeric foams of the present invention useful as absorbents have dry basis density values in the range of from about 0.010 to about 0.018 g/cc, preferably from about 0.013 to about 0.018 g/cc.

Suitable absorbent foams will in general exhibit especially desirable and useful aqueous fluid handling and absorbency characteristics. In particular, when the foam is used as the primary distribution material in an absorbent core of the present invention, the ability to move fluid from the crotch region of the core to the front and/or rear regions of the core is important. The fluid handling and absorbency characteristics that are most relevant for fluid distribution foams are: A) the rate of vertical wicking of fluid through the foam structure, and B) the absorbent capacity of the foam at specific referenced wicking heights. Another important property of foams is their ability to drain (partition) fluid from competing absorbent structures with which the foam can be in contact.

Vertical wicking, i.e., fluid wicking in a direction opposite from gravitational force, is an especially desirable performance attribute for absorbent foams herein. These foams will frequently be utilized in absorbent articles in a manner such that fluid to be absorbed must be moved within the article from a relatively lower position to a relatively higher position within the absorbent core of the article. Accordingly, the ability of these foams to wick fluid against gravitational forces is particularly relevant to their functioning as absorbent materials in the present absorbent articles.

The vertical wicking absorbent capacity test measures the amount of test fluid per gram of absorbent foam that is held within each one inch (2.54 cm) vertical section of the same standard size foam sample used in the vertical wicking test. Such a determination is generally made after the sample has been allowed to vertically wick test fluid to equilibrium (e.g., after about 18 hours). The vertical wicking absorbent capacity test is described in greater detail in the Test Methods Section, infra.

Another important property of absorbent foams useful in the cores of the present invention is their capillary absorption pressure. Capillary absorption pressure refers to the ability of the foam to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h. To be especially useful in absorbent articles for absorbing aqueous fluids, the preferred absorbent foams useful herein will generally have a capillary absorption pressure of at least about 24 cm. (Foams useful herein typically have an absorption pressure of at least about 30 cm, more preferably at least about 40 cm.)

In those embodiments where the distribution material is not particularly suitable for storage of absorbed fluids, the absorbent core will also comprise a material, or combination of materials, whose primary function is the storage of absorbed fluids. The fluid storage material(s) acts to store body exudates away from the wearer's body so as to leave the wearer with a feeling of dryness. The storage materials are maintained in fluid contact with the distribution material (s) such that urine or other aqueous body fluids absorbed by the distribution material can be desorbed by the fluid storage material. When the storage materials are positioned in the front and/or rear regions of the absorbent core, the core provides the fit benefits by storing a majority of the absorbed fluid away from the article's crotch region.

Any material capable of desorbing the distribution material may be utilized as the storage material. For example, the storage material may comprise hydrogel-forming polymers that are water-insoluble, but water-swellable and are capable of absorbing large quantities of fluids. Such polymers are commonly referred to as "hydrocolloids" or "superabsorbent" materials, and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful herein have a multiplicity of anionic, functional groups, such as sulfonic acid, and more typically carboxy groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the hydrogel-forming absorbent polymers. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al), issued Feb. 28, 1978, and in U.S. Pat. No 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076, 663, U.S. Pat. No. 4,093,776, U.S. Pat. No. 4,666,983, and U.S. Pat. No. 4,734,478.

Most preferred polymer materials for use herein are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e. poly (sodium acrylatelacrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

Hydrogel-forming polymers may optionally be combined with fibrous materials to form the storage material. The fibrous materials facilitate, inter alia, uptake of fluid by the hydrogel-forming polymer. Nonetheless, it may be preferred to use relatively high concentrations of hydrogel-forming polymer, while at the same time avoiding the gel blocking phenomena exhibited by many hydrogel-forming polymers. The use of high concentration hydrogel-forming polymers is described in detail in U.S. Pat. No. 5,599,335 (Goldman et al.) and U.S. Pat. No. 5,562,646 (Goldman et al.), both of which are incorporated by reference herein.

Storage materials comprising hydrogel-forming polymers can also comprise fibrous materials to form fibrous web or fibrous matrices. Fibers useful herein include those that are naturally occurring fibers (modified or unmodified), as well as synthetically made fibers. Examples of suitable unmodified/modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely synthetic fibers, or any compatible combination of naturally occurring and synthetic fibers.

The fibers used can be hydrophilic, hydrophobic or can be a combination of both hydrophilic and hydrophobic fibers. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled *Contact Angle, Wettability and Adhesion*, edited by Robert F. Gould (Copyright 1964). A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions normally co-existing. Conversely, a fiber or surface is considered to be hydrophobic if the contact angle is greater than 90° and the fluid does not spread spontaneously across the surface of the fiber.

For storage materials useful herein, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like. For reasons of availability and cost, cellulosic fibers, in particular wood pulp fibers, are preferred for use in the present invention.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

A desirable source of hydrophilic fibers for use in the present invention is chemically stiffened cellulosic fibers. As used herein, the term "chemically stiffened cellulosic fibers" means cellulosic fibers that have been stiffened by chemical means to increase the stiffiess of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., USA; latexes; wet strength resins such as polyamide-epichlorohydrin resin (e.g., Kymene® 557H, Hercules, Inc. Wilmington, Del. USA), polyacrylamide resins described, for example, in U.S. Pat. No. 3,556,932 (Coscia et al), issued Jan. 19, 1971; commercially available polyacrylamides marketed by American Cyanamid Co., Stamford, Con. USA, under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilization of intrafiber crosslink bonds to chemically stiffen the fiber is preferred, it is not meant to exclude other types of reactions for chemical stiffening of the fibers.

Fibers stiffened by crosslink bonds in individualized form (i.e., the individualized stiffened fibers, as well as processes for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al.), issued Jul. 12, 1977. More preferred stiffened fibers are disclosed in U.S. Pat. No. 4,822,453 (Dean et al), issued Apr. 18, 1989; U.S. Pat. No. 4,888,093 (Dean et al), issued Dec. 19, 1989; U.S. Pat. No 4,898,642 (Moore et al), issued Feb. 6, 1990; and U.S. Pat. No. 5,137,537 (Herrow et al), issued Aug. 11, 1992, all of which are incorporated by reference.

In the more preferred stiffened fibers, chemical processing includes intrafiber crosslinking with crosslinking agents while such fibers are in a relatively dehydrated, defibrated (i.e., individualized), twisted, curled condition. Suitable chemical stiffening agents are typically monomeric crosslinking agents including, but not limited to, $C_2$–$C_8$ dialdehyde, $C_2$–$C_8$ monoaldehydes having an acid functionality, and especially $C_2$–$C_9$ polycarboxylic acids. These compounds are capable of reacting with at least two hydroxyl groups in a single cellulose chain or on proximately located cellulose chains in a single fiber. Specific examples of such crosslinking agents include, but are not limited to, glutaraldehyde, glyoxal, formaldehyde, glyoxylic acid, oxydisuccinic acid and citric acid. The effect of crosslinking under these conditions is to form fibers that are stiffened and which tend to retain their twisted, curled configuration during use in the thermally bonded absorbent structures herein. Such fibers, and processes for making them, are described in the above incorporated patents.

The preferred stiffened fibers that are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in U.S. Pat. No. 4,898,642.

The preferred stiffened fibers will have an average dry fiber twist count of at least about 2.7, preferably at least about 4.5 twist, nodes per millimeter. Furthermore, the average wet fiber twist count of these fibers should preferably be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, these preferred stiffened fibers are also curled. Fiber curl can be described as the fractional shortening of the fiber due to kinks, twists, and/or bends in the fiber. For the purposes of the present invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

$$\text{Curl Factor} = (L_A/L_R) - 1$$

An image analysis method that can be utilized to measure $L_R$ and $L_A$ is described in U.S. Pat. No. 4,898,642. Preferably the stiffened fibers will have a curl factor of at least about 0.30, and more preferably will have a curl factor of at least about 0.50.

These chemically stiffened cellulosic fibers have certain properties that make them particularly useful in certain absorbent members according to the present invention, relative to unstiffened cellulosic fibers. In addition to being hydrophilic, these stiffened fibers have unique combinations of stiffness and resiliency. This allows thermally bonded absorbent structures made with these fibers to maintain high levels of absorptivity, and to exhibit high levels of resiliency and an expansionary responsiveness to wetting. In particular, the resiliency of these stiffened fibers enables the absorbent member to better maintain its capillary structure in the presence of both fluid and compressive forces normally encountered during use and are thus more resistant to collapse.

A preferred storage material for practicing the present invention comprises polymeric foam material derived from HIPEs. These materials will preferably have sufficient absorption pressures to desorb the distribution material, thereby providing reduced fluid storage in the crotch region of the article. However, as indicated, a single material may function as both the distribution and storage material in the present articles.

The foams described above with respect to the distribution component of the present absorbent articles are also useful as the storage component of the articles. Particularly preferred are collapsible polymeric foam materials that, upon contact with aqueous fluids (in particular aqueous body fluids such as urine), can expand and absorb these fluids.

These absorbent polymeric storage foam materials comprise a hydrophilic, flexible, nonionic polymeric foam structure of interconnected open-cells as disclosed in, for example, U.S. Pat. No. 5,387,207 (Dyer et al.), issued Feb. 7, 1995, and copending U.S. patent application Ser. No. 08/563,866 (DesMarais et al.), filed Nov. 25, 1995, the disclosure of each of which is hereby incorporated by reference.

The storage foam material useful in the present invention provides very low density absorbent foams. For a given expanded thickness, these lower density foams more efficiently utilize the available polymer material. As a result, the lower density absorbent foams provide an economically attractive means for achieving thinner absorbent cores for absorbent articles such as diapers, adult incontinence pads or briefs, sanitary napkins, and the like. This is achieved while providing desired absorbency and mechanical properties.

The materials utilized in the absorbent core of the present articles may be arranged in a variety of ways, so long as the requisite distribution material is included in the crotch region. As discussed above, it is preferred to have relatively little fluid storage in the crotch region. Thus, while storage materials that do not function to distribute fluid may be present in the crotch region of the absorbent core, the primary material of the crotch region will be distribution or redistribution/storage material.

Figure 5:
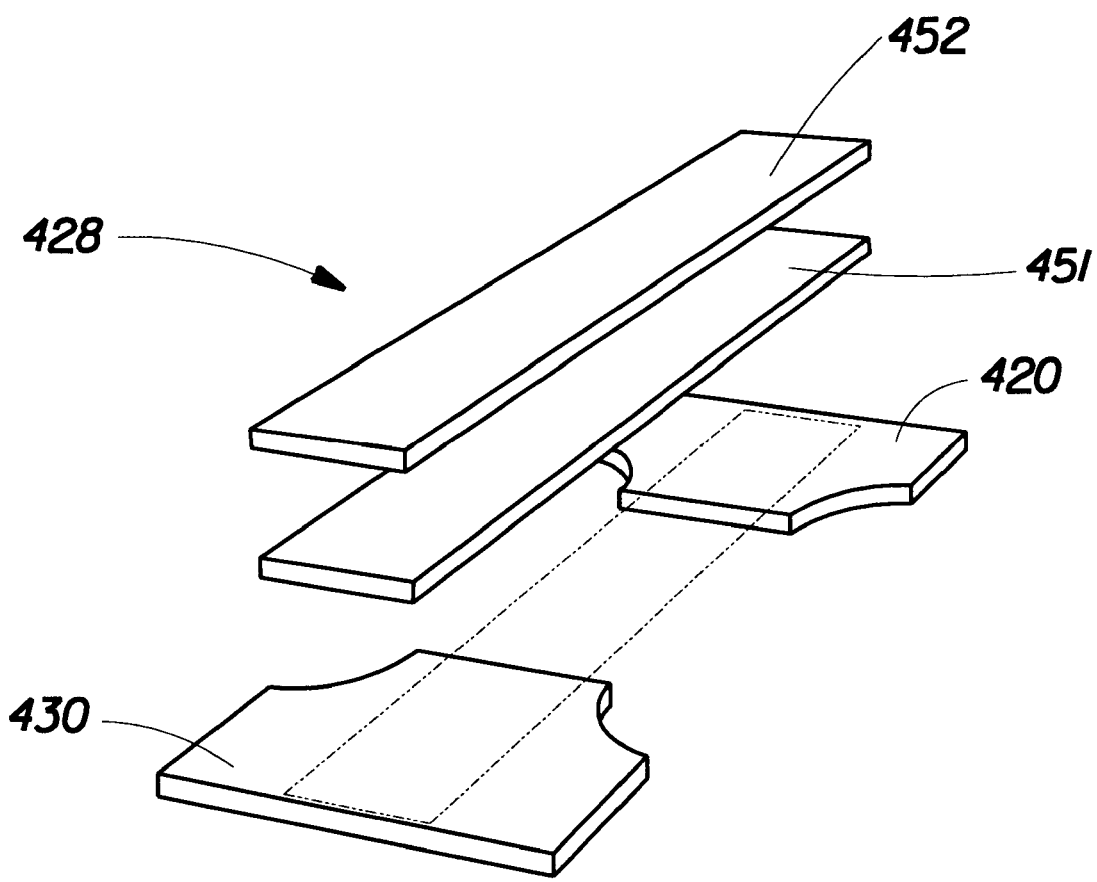
FIG. 5 is a blown apart perspective view of a multipiece absorbent core of the present invention.

The absorbent cores useful herein may comprise separate components for use in the crotch, front and rear portions of the absorbent core. FIG. 5 shows an exploded perspective view depicting the elements of an absorbent core 428. As depicted in FIG. 5, the absorbent core 428 comprises a front panel 420 and a back panel 430, both made of absorbent material, preferably material suitable for fluid storage. FIG. 5 further shows a center section 451 of absorbent material overlying the front and back panels 420 and 430. The material of this center section 451 comprises a fluid distribution material having the vertical wicking absorbent capacities discussed above, or a material having requisite distribution and storage properties.

Center section 451 may comprise multiple strips of absorbent material, each having individual shape, width, length and thickness characteristics. For example, in a preferred embodiment, a relatively thin, flexible, resilient, polymeric foam strip 451 is preferably made from the same fluid distribution/storage material as the front and back panels 420 and 430. Also depicted in FIG. 5 is an acquisition material 452.

TEST METHODS

A. ARTICLE TOTAL ABSORBENT CAPACITY AND CROTCH REGION % CAPACITY

The following protocol is intended to provide the Total Absorbent Capacity ("TAC") as well as, the Crotch Region Capacity ("CRC") of the article. The protocol uses data determined from in-use testing of test articles by panelists.

Panelist Selection

Panelists should be recruited by weight, within the intended size range of the articles being tested. Currently, the article sizes and baby weights for marketed Pampers, Luvs and Huggies are as follows (as of Mar. 25, 1997):

| Diaper Size | Newborn | Small | Small/Medium | Medium | Large | X-Large |
| --- | --- | --- | --- | --- | --- | --- |
| Pampers | up to 10 lbs | 8–14 lbs | 12–18 lbs | 16–28 lbs | over 22 lbs | over 27 lbs |
| Luvs | na | 8–15 lbs | 12–18 lbs | 16–28 lbs | 21–37 lbs | over 30 lbs |
| Huggies | up to 10 lbs | 8–14 lbs | 12–18 lbs | 16–28 lbs | 22–37 lbs | over 30 lbs |

A group of 100 panelists should be recruited uniformally across the appropriate weight range relative to the size of articles being tested and the intended user group.

Note: the above sizes are for currently marketed articles and may change as article designs and or sizes are modified.

Following the recruiting step, 30 panelists are to be selected from the group at random.

Article Set-up

The test articles are weighed to provide a dry article weight.

The panelist removes the article the child is wearing when the test begins, i.e. the panelist's own article, and the panelist applies the test article in the panelist's normal fashion.

Once the test article is applied, the panelist places the wearer in the standing position and the crotch point is determined as previously described in this application.

The crotch point is then marked on the outside of the test article in a permanent fashion.

The loading zone is then determined by measuring from the crotch point forward to the appropriate genital point relative to the sex and size of the wearer. The distance forward from the crotch point for females in the medium size is 1.25 inches. The distance forward from the crotch point for males in the medium size range is 2.5 inches.

It is apparent to one skilled in the art that these distances may increase or decrease with the size of the wearer. Therefor, for the other sizes, the distance can be determined by placing the wearer in a standing position and determining the crotch point as specified previously, and then measuring from the crotch point to the urethra or base of the penis.

Once the loading zone is determined, the distance from the front waist to the loading zone is measured; this distance is used to establish the length of the loading tube to be inserted into the article during the synthetic urine loading.

Synthetic Urine

The test fluid to be used for the test is synthetic urine (syn-urine). This aqueous composition comprises the following components dissolved in distilled water:

| Component | Percentage |
|---|---|
| KCl | 2.0 g/L |
| Na$_2$SO$_4$ | 2.0 g/L |
| (NH$_4$)$_2$HPO$_4$ | .85 g/L |
| (NH$_4$)$_2$HPO$_4$ | .15 g/L |
| CaCl$_2$ | .19 g/L |
| MgCl$_2$ | .23 g/L |

The temperature in the syn-urine bath is to be held at 37° C. A suitable heated bath is Lauda M20-B available from VWR Scientific Products.

Delivery pumps are to be used to pump the syn-urine from the heated bath to the article. The volume and rate of delivery is to be 75 ml at 15 mls/sec. Suitable pumps include Masterflex Models 7550-60 or 7524-00 available from Cole Parmer Instrument Company. The inner diameter of the loading tube is to be 0.125 inch.

Protocol

Once the articles are applied and marked as described above, loose fitting blue cotton pants are weighed to provide a dry pants weight and then the pants are applied over the test article so that leakage can be easily identified and measured.

The test articles are then loaded by inserting the loading tube to the predetermined distance, as measured from the waist, and applying the specified loading at the specified rate.

Between loads, the wearers return to normal activity.

The articles are loaded with the specified load and rate every 10 minutes, i.e. 10 minute intervals between loads. Prior to each loading, the cotton pants are checked for leakage.

These loadings are continued until about 1 gram of fluid leaks from the article onto the cotton pants. This can be determined by removing the pants and weighing them.

Once 1 gram of fluid has leaked onto the pants, the test article is removed and immediately weighed.

Total Capacity and Crotch Region Capacity

The total capacity for a given test article is determined by subtracting the dry article weight of the given article from the wet article weight of that same article.

The total capacity for the group is the average of the total capacities of the individual articles.

Crotch region capacity is determined by laying the loaded article flat and cutting the crotch region out of the article. (The crotch region is determined relative to the crotch point which was previously identified for the article.) This region is then weighed. This procedure should be conducted within 15 minutes of removal of the article from the wearer article A corresponding crotch region is cut from a dry article to provide a dry crotch region weight.

The crotch capacity is determined by subtracting the dry crotch region weight from the wet crotch region weight. This provides the crotch capacity for a given article.

The crotch capacity for the group of articles is considered to be the average of the individual crotch region capacities.

The crotch region capacity as a percent of the total is determined by dividing the average crotch region capacity by the average total capacity for a given set of articles.

B. FLUID ACQUISITION

The fluid acquisition method provides a means for introducing fluid into an absorbent article that simulates in-use conditions. The article will be loaded to 70% of its total absorbent capacity (determined in Section A). Certain of the other Test Methods described below will utilize an article wetted according to this method for characterization in accordance with the present invention.

PRINCIPLE

This test simulates the introduction of urine into an article under the following conditions:

1) A pressure of 0.4 psi (about 28 g/cm$^2$) is applied to an article sample.

2) Synthetic urine is introduced to the article in 50 ml/load increments at a rate of 10 ml/sec, with a 5 minute time period (equilibration time) between each loading. The number of loads will be dictated by the total absorbent capacity of the article.

APPARATUS

| | |
|---|---|
| Conditioned Environment: | Temperature and humidity controlled within the following limits: Temperature: 88 ± 2° F. Relative Humidity: 50 ± 2% |
| Acquisition Tester: | Obtain from Concord - Renn Co., 6315 Warrick St., Cincinnati, OH. 45227. Part |
| | Test Bed (PLEXIGLAS) Foam Base - 6" × 20" × 1" foam covered with polyethylene backsheet material - foam type: Density 1.0 lb/ft$^3$ IDL 24 psi Nozzle Coverplate |
| Graduated cylinders: (100 ml) (1,000 ml) | VWR Scientific, (100 ml) Catalog number: 24711-310 (1,000 ml) Catalog number: 24711-364 or equivalent |
| Erlenmeyer flask: (6,000 ml) | VWR Scientific Catalog number: 29135-307 or equivalent |
| Digital Pump: | Cole-Parmer Instrument Co.; Tel. No. (800) 323-4340 Catalog number: g-07523-20 |
| Easy Load Pump Head: | Cole-Parmer Instrument Co. Catalog number: g-07518-02 |
| Distilled water: | Convenient source |
| Synthetic Urine: | Synthetic urine as prepared in Test Method section A. |

ASSEMBLY OF TEST APPARATUS

Figure 6:
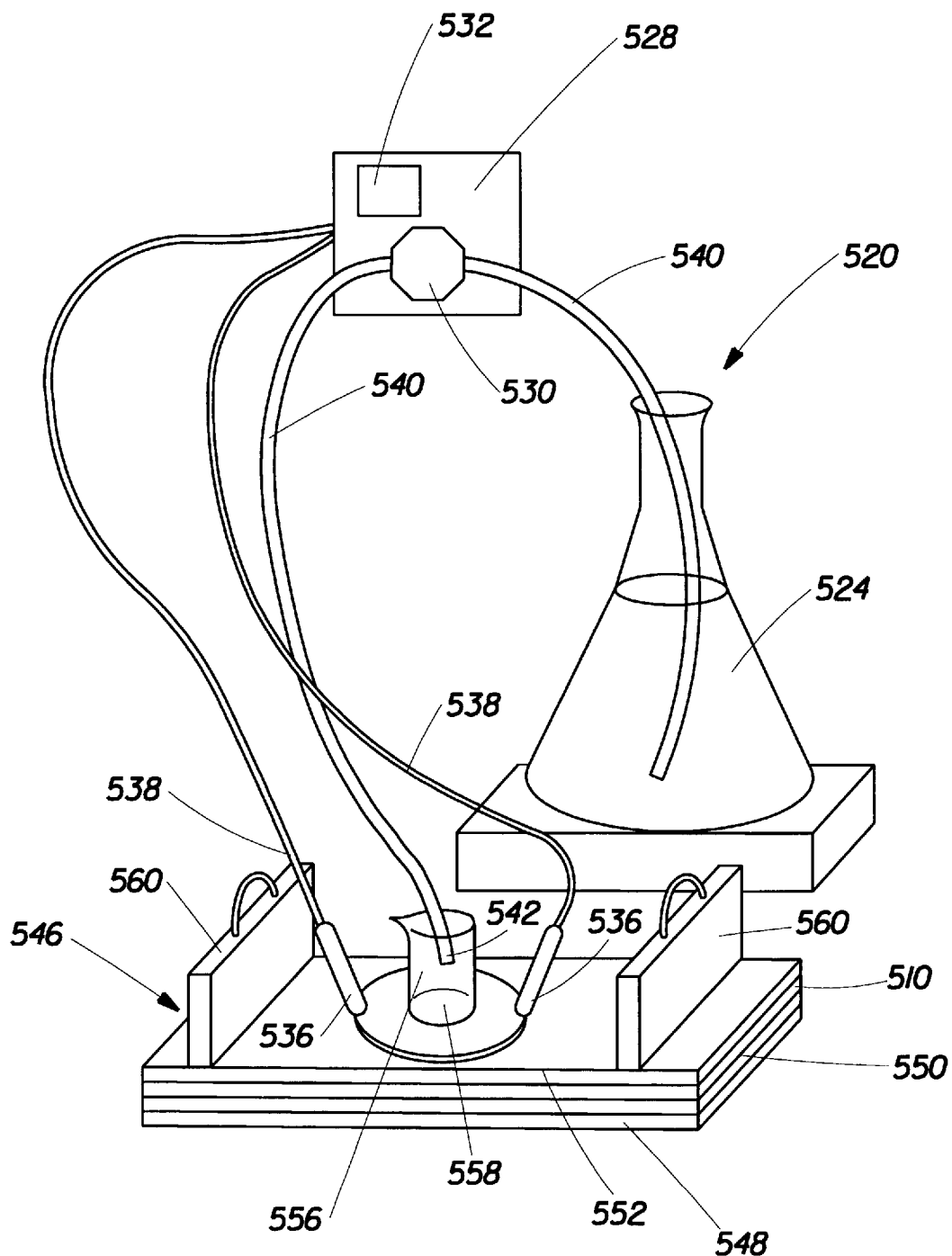
FIG. 6 is a schematic view of the apparatus used to load articles for characterization according to other procedures discussed in the Test Method section.

The test apparatus should be assembled as shown in FIG. 6. The test apparatus is designated by reference number 520. The test apparatus 520 is placed on a suitable table or bench top. The test apparatus 520 comprises a supply of synthetic urine 524, a pump 528, a pair of electrical connectors (or probes) 536, and a sample holder 546.

The pump 528 is a volumetric pump which is equipped with a pump head 530 and digital timer 532. The electrical probes 536 are connected to the pump 528 by wires 538. Tygon® tubing 540 runs from the supply of synthetic urine 524 to the pump 528 and from the pump 528 to the sample holder 546. The Tygon® tubing 540 that runs from the pump 528 to the sample holder 546 is preferably held over the sample holder 546 by a ring stand (not shown). The end of the Tygon® tubing 540 that runs to the sample holder 546 also contains a nozzle 542 for directing the synthetic urine onto the test sample.

The sample holder 546 comprises a PLEXIGLAS test bed, a foam base 550, and a cover plate 552. The test bed 548 is shown schematically in FIG. 6 as comprising a PLEXIGLAS base plate for simplicity. The test bed 548 should also have four PLEXIGLAS walls which stand upright from the base and surround the diaper sample 510. This prevents synthetic urine from running out of the test bed 548 during the test. The foam base 550 is placed on top of the PLEXIGLAS base plate 548 so that the pressure on the sample will be equalized during the test. A diaper sample 510 is placed on the foam base with its topsheet facing upward. The cover plate 552 is then placed on top of the diaper sample so that the cylindrical liquid directing column 556 and opening 558 in the cover plate are in the transverse center of the diaper sample. Weights 560 are then placed on the cover plate 552 so that a pressure of 0.4 psi is applied to the diaper sample.

The electrical probes 536 are arranged so that they just touch the topsheet of the diaper sample in the region where synthetic urine is deposited. The electrical probes are located outside, and on opposite sides of the cylindrical liquid directing column 556. The electrical probes 536 detect the presence of synthetic urine on the topsheet of the diaper sample. When all of the synthetic urine has been acquired by the diaper sample, the electrical connection between the electrical probes 536 will be broken.

PROCEDURE

1) Cut any elastics out of the test diaper so that the diaper will lay flat. Place the diaper on top of the piece of foam in the acquisition tester base. The diaper should be placed with the topsheet of the diaper facing upward, so that the synthetic urine will be applied to the topsheet. The diaper should be positioned so the urine delivery nozzle is approximately 3 inches from the front edge of the diaper.
2) Place the cover plate assembly on the diaper.
3) Gently place the appropriate weights on the cover plate so that a pressure of 0.4 psi is placed on the diaper.
4) Move the ring stand into position so that the nozzle is directly above the center of the cylindrical liquid directing column. Lower the ring until the nozzle extends 2 inches (about 5 cm) above the surface of the diaper. Position the nozzle so that it is perpendicular to the bench top.
5) Start the pump.
6) The pump will begin dispensing the specified volume of synthetic urine, and the timer will run until that volume has been absorbed by the diaper.
7) After the fluid has been absorbed, the confining pressure is removed, leaving the cover plate in place, for a period of 5 minutes. The confining pressure is then reapplied for the remaining 10 minutes of the equilibration time.
8) After the 15 minute equilibration time has elapsed, the test cycle will automatically repeat. The test cycle will run the desired number of times so that a specific volume of synthetic urine is applied to the diaper sample.
9) After completing all of the tests, run distilled water through the tubing. Clean the surface of the small probe contacts located inside the base of the top plate tube with a small brush on a daily basis. If the acquisition tester is being used around the clock and it is not possible to rinse the synthetic urine out of the tubing, replace the tubing monthly. Replace the foam base every 3 months to maintain firmness of support.

C. CROTCH WIDTH WHEN WET AND DRY CROSS SECTIONAL AREA

The crotch width of an absorbent core of an absorbent article is measured by first determining the crotch point of the absorbent article. The article is then wetted to 70% of it's total capacity in accordance with the Fluid Acquisition method. The article is removed from the apparatus and is allowed to equilibrate for 1 hour. Upon equilibration, the article is cut transversely through its thickness to provide a two (2) inch long section, where the crotch point is at the tranverse and longitudinal center of the section. Each of the wetted layers of the sectioned sample are then weighed. The width of the layer containing the most absorbed fluid corresponds to the crotch width of the absorbent core.

Once the above determination has been made of the layer of the absorbent core that retains the most fluid, a dry article is cut transversely per the preceding paragraph. The layer previously determined to retain the most fluid is separated from the other absorbent core components and the dry caliper and width are determined. (Caliper is measured under a confining pressure of 0.2 psi.) When this layer consists of a plurality of discrete layers, the width and caliper of each of the layers is measured and the sum of their individual cross sectional areas corresponds to the crotch region cross sectional area of the absorbent core.

D. VERTICAL WICKING RATE AND VERTICAL WICKING ABSORBENT CAPACITY

A material's vertical wicking rate at 5 cm and the material's vertical wicking absorbent capacity for a given height is measured using the Vertical Wicking Rate and Vertical Wicking Absorbent Capacity Test described in the TEST METHODS section of U.S. Pat. No. 5,387,207 (Dyer et al), which is incorporated by reference, except at 31° C. rather than 37° C. For materials that lack sufficient integrity to withstand the testing protocol, a hydrophobic screen that does not impact wicking performance can be used to support the material. Finally, the washing and redrying step in the '207 is not performed.

As set forth in pertinent part in U.S. Pat. No. 5,387,207, vertical wicking rate and vertical wicking absorbent capacity are measures of the ability of a dry foam to wick fluid vertically from a reservoir. The time required for the fluid front to wick through a 5 cm vertical length of a strip of foam is measured to give a vertical wicking rate. After fluid wicks to its equilibrium height, the amount of fluid held by the foam strip at a particular vertical wicking height is determined to give a vertical wicking absorbent capacity.

Jayco synthetic urine colored with blue food coloring is used in the following methods to determine vertical wicking rate and vertical wicking absorbent capacity. In this test procedure, the materials are equilibrated at 31° C. and the test is performed at the same temperature.

A strip of foam approximately 70 cm long X 2 cm wide X 0.25 cm thick is supported vertically with one end immersed 1 to 2 mm into a reservoir of synthetic urine. The liquid is allowed to wick up the foam strip to its equilibrium height (e.g., about 18 hours), which should be less than the sample length. During this procedure, the sample should be shielded, for example with a capped glass cylinder, to prevent evaporation.

The time needed to wick 5 cm is used as a measure of vertical wicking rate.

The sample is quickly removed and placed on a non-absorbent surface where it is cut into 1 inch (2.54 cm) pieces using a tool sharp enough not to compress the foam sample. Each piece is weighed., and the absorbent capacity is calculated for each piece.

What is claimed is:

1. An absorbent core having a crotch region, wherein (i) the crotch region has an absorbent capacity of not more than about 40% of the absorbent core's total absorbent capacity and (ii) the crotch region comprises a material having a vertical wicking capacity of at least about 15 g/g at a height of 2 cm.

2. The absorbent core of claim 1 wherein the crotch region of the absorbent core has an absorbent capacity of not more than about 25% of the absorbent core's total absorbent capacity.

3. The absorbent core of claim 2 wherein the crotch region of the absorbent core has an absorbent capacity of not more than about 15% of the absorbent core's total absorbent capacity.

4. The absorbent core of claim 3 wherein the crotch region of the absorbent core has an absorbent capacity of from 0 to about 10% of the absorbent core's total absorbent capacity.

5. The absorbent core of claim 1 wherein the material has a vertical wicking capacity of at least about 25 g/g at a height of 2 cm.

6. The absorbent core of claim 5 wherein the material has a vertical wicking capacity of at least about 40 g/g at a height of 2 cm.

7. The absorbent core of claim 1, wherein the crotch region comprises an open-celled absorbent polymeric foam having a specific surface area per foam volume value of at least about 0.025 $m^2$/cc.

8. The absorbent core of claim 1, wherein the crotch region comprises an open-celled absorbent polymeric foam having a resistance to compression deflection of about 40% or less when measured under a confining pressure of 0.74 psi.

9. The absorbent core of claim 8, wherein the polymeric foam has a resistance to compression deflection of from about 2% to about 25% when measured under a confining pressure of 0.74 psi.

10. The absorbent core of claim 1, wherein the crotch region comprises an open-celled absorbent polymeric foam having a capillary absorption pressure of at least about 24 cm.

11. An absorbent article comprising a backsheet, and the absorbent core of claim 1 positioned above said backsheet.

12. An absorbent core having a crotch region, wherein (i) the crotch region has an absorbent capacity of not more than about 40% of the absorbent core's total absorbent capacity and (ii) the crotch region comprises a material having a vertical wicking capacity of at least about 10 g/g at a height of 20 cm.

13. The absorbent core of claim 12 wherein the crotch region of the absorbent core has an absorbent capacity of not more than about 25% of the absorbent core's total absorbent capacity.

14. The absorbent core of claim 13 wherein the crotch region of the absorbent core has an absorbent capacity of not more than about 15% of the absorbent core's total absorbent capacity.

15. The absorbent core of claim 14 wherein the crotch region of the absorbent core has an absorbent capacity of from 0 to about 10% of the absorbent core's total absorbent capacity.

16. The absorbent core of claim 12 wherein the material has a vertical wicking capacity of at least about 20 g/g at a height of 20 cm.

17. The absorbent core of claim 16 wherein the material has a vertical wicking capacity of at least about 30 g/g at a height of 20 cm.

18. The absorbent core of claim 17 wherein the material has a vertical wicking capacity of at least about 40 g/g at a height of 20 cm.

19. An absorbent article comprising a backsheet, and the absorbent core of claim 12 positioned above said backsheet.

20. An absorbent core having a crotch region, wherein (i) the crotch region has an absorbent capacity of not more than about 40% of the absorbent core's total absorbent capacity and (ii) the crotch region comprises a material having a vertical wicking capacity at a height of 25 cm of at least about 5 g/g.

21. The absorbent core of claim 20 wherein the crotch region of the absorbent core has an absorbent capacity of not more than about 25% of the absorbent core's total absorbent capacity.

22. The absorbent core of claim 21 wherein the crotch region of the absorbent core has an absorbent capacity of not more than about 15% of the absorbent core's total absorbent capacity.

23. The absorbent core of claim 22 wherein the crotch region of the absorbent core has an absorbent capacity of from 0 to about 10% of the absorbent core's total absorbent capacity.

24. The absorbent core of claim 20 wherein the material has a vertical wicking capacity of at least about 15 g/g at a height of 25 cm.

25. The absorbent core of claim 24 wherein the material has a vertical wicking capacity of at least about 20 g/g at a height of 25 cm.

26. The absorbent core of claim 25 wherein the material has a vertical wicking capacity of at least about 30 g/g at a height of 25 cm.

27. An absorbent article comprising a backsheet, and the absorbent core of claim 9 positioned above said backsheet.

28. An absorbent core having a cross sectional area at the core's crotch point of not more than about 2.6 cm$^2$, wherein the crotch region comprises a material having a vertical wicking capacity of at least about 10 g/g at a height of 20 cm.

29. The absorbent core of claim 28 wherein the absorbent core has a crotch cross sectional area at the core's crotch point of not more than about 1.8 cm$^2$.

30. The absorbent core of claim 29 wherein the absorbent core has a crotch cross sectional area at the core's crotch point of not more than about 1 cm$^2$.

31. An absorbent article comprising a backsheet, and the absorbent core of claim 28 positioned above said backsheet.

32. An absorbent core having a crotch region, wherein (i) the crotch region has an absorbent capacity of not more than about 40% of the absorbent core's total absorbent capacity and (ii) the crotch region comprises a material having a vertical wicking capacity at a height of 30 cm of at least about 0.5 g/g.

33. The absorbent core of claim 32 wherein the crotch region of the absorbent core has an absorbent capacity of not more than about 25% of the absorbent core's total absorbent capacity.

34. The absorbent core of claim 33 wherein the crotch region of the absorbent core has an absorbent capacity of not more than about 15% of the absorbent core's total absorbent capacity.

35. The absorbent core of claim 34 wherein the crotch region of the absorbent core has an absorbent capacity of from 0 to about 10% of the absorbent core's total absorbent capacity.

36. The absorbent core of claim 32 wherein the material has a vertical wicking capacity of at least about 10 g/g at a height of 30 cm.

37. The absorbent core of claim 36 wherein the material has a vertical wicking capacity of at least about 20 g/g at a height of 30 cm.

38. The absorbent core of claim 37 wherein the material has a vertical wicking capacity of at least about 30 g/g at a height of 25 cm.

39. An absorbent article comprising a backsheet, and the absorbent core of claim 32 positioned above said backsheet.

40. An absorbent core having a crotch region, wherein the crotch region has an absorbent capacity of not more than about 40% of the absorbent core's total absorbent capacity and wherein the core comprises an open-celled absorbent polymeric foam material having a specific surface area per foam volume value of at least about 0.025 m$^2$/cc.

41. The absorbent core of claim 40, wherein the polymeric foam material has a specific surface area per foam volume value of at least about 0.05 m$^2$/cc.

42. The absorbent core of claim 41, wherein the polymeric foam material has a specific surface area per foam volume value of at least about 0.07 m$^2$/cc.

43. The absorbent core of claim 40, wherein the open-celled absorbent polymeric foam has a resistance to compression deflection of about 40% or less when measured under a confining pressure of 0.74 psi.

44. The absorbent core of claim 43, wherein the polymeric foam has a resistance to compression deflection of from about 2% to about 25% when measured under a confining pressure of 0.74 psi.

45. The absorbent core of claim 44, wherein the polymeric foam has a resistance to compression deflection of from about 2% to about 15% when measured under a confining pressure of 0.74 psi.

46. The absorbent core of claim 40, wherein the open-celled absorbent polymeric foam has a capillary absorption pressure of at least about 24 cm.

47. The absorbent core of claim 46, wherein the open-celled absorbent polymeric foam has a capillary absorption pressure of at least about 30 cm.

48. An absorbent article comprising a backsheet, and the absorbent core of claim 40 positioned above said backsheet.

* * * * *

UNITED STATES PATENT AND TRADEMARK OFFICE
CERTIFICATE OF CORRECTION

| | | |
|---|---|---|
| PATENT NO. | : 6,015,935 | |
| APPLICATION NO. | : 08/825071 | |
| DATED | : January 18, 2000 | |
| INVENTOR(S) | : LaVon et al. | |

It is certified that error appears in the above-identified patent and that said Letters Patent is hereby corrected as shown below:

Column 9
Line 2, please delete "Similary" and insert therefor --Similarly--.
Line 3, please delete "lonitudinal" and insert therefor --longitudinal--.
Column 11
Line 26, please delete "open-called" and insert therefor --open-celled--.
Column 16
Line 37, please delete "acrylatelacrylic" and insert therefor --acrylate/acrylic--.
Column 17
Line 33, please delete "polyurcthanes" and insert therefor --polyurethanes--.
Line 49, please delete "stiffiess" and insert therefor --stiffness--.
Line 64, after "Con.", please insert "," (a comma).
Column 19
Line 12, please delete "andlor" and insert therefor --and/or--.
Column 21
Line 48 ($3^{rd}$ line under "Component"), please delete "$(NH_4)_2HPO_4$" and insert therefor --$(NH_4)_2H_2PO_4$--.
Column 22
Line 27, please delete second occurrence of "article".
Line 27, after "wearer", please insert "." (a period).

UNITED STATES PATENT AND TRADEMARK OFFICE
CERTIFICATE OF CORRECTION

PATENT NO. : 6,015,935
APPLICATION NO. : 08/825071
DATED : January 18, 2000
INVENTOR(S) : LaVon et al.

It is certified that error appears in the above-identified patent and that said Letters Patent is hereby corrected as shown below:

Column 23
Please delete entire table beginning at line 1 and insert therefor
--APPARATUS

| | |
|---|---|
| Conditioned Environment: | Temperature and humidity controlled within the following limits: |
| | Temperature: 88 ± 2°F |
| | Relative Humidity: 50 ± 2% |
| Acquisition Tester: | Obtain from: |
| | Concord - Renn Co. |
| | 6315 Warrick St. |
| | Cincinnati, OH. 45227. |
| | Part |
| | Test Bed (PLEXIGLAS) |
| | Foam Base - 6" x 20" x 1" foam covered with polyethylene backsheet material - foam type: Density 1.0 lb/ft$^3$. IDL 24 psi |
| | Nozzle |
| | Cover plate |
| Graduated cylinders: (100ml) (1,000 ml) | VWR Scientific, (100 ml) Catalog number: 24711-310 (1,000 ml) Catalog number: 24711-364 or equivalent |
| Erlenmeyer flask: (6,000 ml) | VWR Scientific Catalog number: 29135-307 or equivalent |
| Digital Pump: | Cole-Parmer Instrument Co.; Tel. No. (800) 323-4340 Catalog number: G-07523-20 |
| Easy Load Pump Head: | Cole-Parmer Instrument Co. Catalog number: g-07518-02 |
| Distilled water: | Convenient source |
| Synthetic Urine: | Synthetic urine as prepared in Test Method section A.-- |

UNITED STATES PATENT AND TRADEMARK OFFICE
CERTIFICATE OF CORRECTION

PATENT NO. : 6,015,935
APPLICATION NO. : 08/825071
DATED : January 18, 2000
INVENTOR(S) : LaVon et al.

It is certified that error appears in the above-identified patent and that said Letters Patent is hereby corrected as shown below:

<u>Column 25</u>
Line 40, please delete "weighed.," and insert therefor --weighed,--.

Signed and Sealed this

Seventeenth Day of October, 2006

JON W. DUDAS
*Director of the United States Patent and Trademark Office*